United States Patent [19]

Lanin et al.

[11] 4,389,905
[45] Jun. 28, 1983

[54] CUTTER FOR COLLECTING A REPRESENTATIVE SAMPLE

[76] Inventors: Semyon Lanin; Vladimir Lanin, both of 330 Wadsworth Ave., Apt. 6F, New York, N.Y. 10040

[21] Appl. No.: 287,144

[22] Filed: Jul. 27, 1981

[51] Int. Cl.[3] .............................................. G01N 1/20
[52] U.S. Cl. .................................................. 73/863.54
[58] Field of Search ........... 73/863.51, 863.54, 863.55, 73/863.56, 863.31

[56] References Cited
U.S. PATENT DOCUMENTS 4,165,645  8/1979  Cooper .......................... 73/863.54

*Primary Examiner*—S. Clement Swisher

[57] ABSTRACT

A sampling cutter for a sampling machine to extract a representative sample of material directly from a conveyor's discharge trajectory stream by having a feed opening for sampling material cleaned off the conveyor and falling separately and distantly from the main stream of material.

5 Claims, 4 Drawing Figures

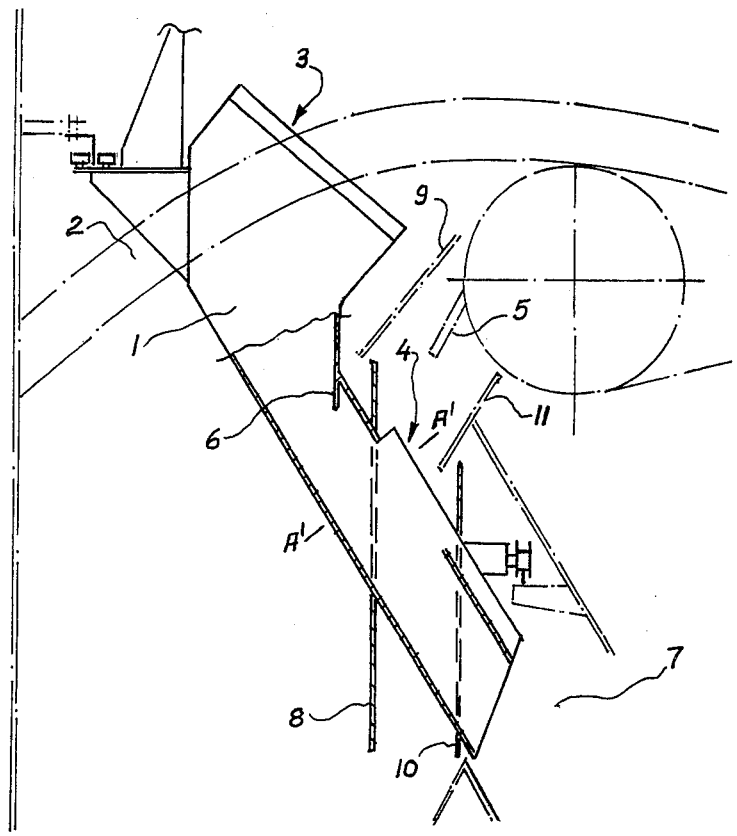
FIG. 1
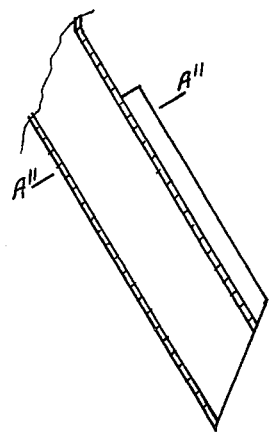
FIG. 3
SECT. A'-A'
FIG. 4
SECT. A"-A"
FIG. 2

CUTTER FOR COLLECTING A REPRESENTATIVE SAMPLE

BACKGROUND OF THE INVENTION

This invention relates mainly to an arrangement for collecting a representative sample directly from a stream of conveyed material that continues on a horisontal flight beyond the conveyor.

At the present time, under such conditions, conventional sampling cutters having a feed opening only on their top extract a sample only from the trajectory of the main stream of material.

Wet fines cleaned off the conveyor fall separately and distantly from the conventional feed opening in the capturing top part of the cutter. The cutter does not take in any part of this material. The worst part of the material that should have been extracted simply goes into the reject chute.

This introduces a bias in final analytical results that is of significant economical importance.

SUMMARY OF THE INVENTION

In accordance with the invention, the cutter has an opening for sampling the main stream of material and also an opening for sampling material cleaned off the conveyor and falling separately and distantly from the main stream. Such an opening is located in the bottom, chute part of the cutter and can be implemented directly in the wall of the cutter so that all material travels together, or can be implemented as a separate trough so that the two streams stay separate.

In order to shield the sampling system from material not extracted by the cutter, a conventional partition is attached, and an additional second partition can be attached to the cutter.

BRIEF DESCRIPTION OF THE DRAWING

Further objects and advantages of the invention will become more apparent from the following description and claims, and from the accompanying drawing wherein:

FIG. 1 is a simplified cross section of a sampling cutter for collecting a representative sample of material.

FIG. 2 is a different version of the chute part of the cutter shown in FIG. 1, on which the partitions (8 and 10 in FIG. 1) have been omitted.

FIG. 3 shows a cross section A'—A' of the cutter shown in FIG. 1; FIG. 4 is the cross section A"—A" of the version of the cutter shown in FIG. 2.

DETAILED DESCRIPTION OF THE PREFERRED EMBODIMENT

FIG. 1 shows cutter 1 intersecting the discharge trajectory 2. This cutter 1 is provided with feed opening 3 in the capturing part of the cutter housing and feed opening 4 in the chute part of the cutter housing. Either or both of these openings may have adjustable lips.

The moveable cutter is supported on wheels on which it may move across the falling material's trajectory. This movement is initiated by a drive, which is not shown.

When the cutter 1 intersects the discharge stream trajectory 2, part of the main stream of the sampled material (an increment) passes inside the cutter 1 through feed opening 3. Material falling separately from the main trajectory 2, i.e. wet fines cleaned off the conveyor by conveyor cleaning device 5, is sampled by feed opening 4, which should be adequately sized.

The cutter 1 may be equipped with baffle plate 6, which prevents the stream of material collected by feed opening 3 from falling out through opening 4 and/or blocking it.

All the material collected by the cutter during intersection of the material stream passes into chute 7 of the sampling system.

Conventional partition 8, which is connected to the moveable cutter, together with stationary partition 9 does not allow arbitrary entrance of material to the sampling chute 7. The cutter 1 can be equipped with partitions 10 and 11 for additional protection from arbitrary entrance of conveyed material into the sampling chute.

The cutter may have a separate path to sampling chute 7 for material collected in the main stream and a separate path for material collected while falling out of the main stream. This version is shown in FIGS. 2 and 4. The difference between the two versions is seen explicitly in a comparison of the sections in FIGS. 3 & 4.

We claim:

1. A sampling cutter for a sampling machine, the cutter having a housing with a first feed opening (3) for direct sampling of material moving in the main discharge trajectory of a stream to be sampled and a chute part for diverting sampled material to a chute (7) of a sampling system, said chute part having a second feed opening (4) for sampling material moving separately from the main stream, means for supporting and moving the cutter through the stream of material to be sampled, and means for preventing arbitrary entrance of conveyed material into the chute (7) of the sampling system.

2. A sampling cutter in accordance with claim 1 wherein the chute part has a wall and the second opening is formed in the wall.

3. A sampling cutter in accordance with claim 2 including a baffle plate (6) within said chute part upstream from the second opening for preventing loss of material sampled at the first opening from the second opening.

4. A sampling cutter in accordance with claim 1 wherein said second feed opening leads to a separate trough on the chute part which leads to the sampling chute.

5. A sampling cutter in accordance with claim 1 wherein said last recited means includes two partitions, one (8) before the second feed opening and the second (10) before the sampling system chute.

* * * * *